Patent Number: 5,273,631
… Date of Patent: Dec. 28, 1993

[54] METHOD FOR CONTINUOUSLY DETERMINING CONCENTRATION OF CHLORIDE IONS AND BROMIDE IONS CONTAINED IN SERUM

[75] Inventors: Hisao Ohsawa; Katsuhide Suzuki, both of Tokyo; Akifumi Yamada, Niigata, all of Japan

[73] Assignee: Nippon Filcon Co., Ltd., Tokyo, Japan

[21] Appl. No.: 914,569

[22] Filed: Jul. 17, 1992

[30] Foreign Application Priority Data

Jul. 19, 1991 [JP] Japan .................................. 3-269959

[51] Int. Cl.⁵ .......................................... G01N 27/404
[52] U.S. Cl. .............................. 204/153.13; 204/412; 204/415
[58] Field of Search .................. 204/153.13, 153.17, 204/405, 412, 415, 434

[56] References Cited

U.S. PATENT DOCUMENTS 3,032,493  5/1962  Coulson et al. ............... 204/405
3,413,199  11/1968  Morrow ........................ 204/153.13
3,756,923  9/1973  Dahms .......................... 204/415
4,132,605  1/1979  Tench et al. .................. 204/434

*Primary Examiner*—T. Tung
*Attorney, Agent, or Firm*—Beveridge, DeGrandi, Weilacher & Young

[57] ABSTRACT

A method is disclosed for determining the concentration of chloride ions and bromide ions employing one and the same serum specimen and one measuring electrode assembly consisting of a working electrode, a counter electrode and a reference electrode which is covered with a polymer film having fine porosity being disposed in a serum specimen. The potential level of the working electrode is cyclically changed within the first predetermined range to determine the total amount of coulombs based on the total amount of chloride ions and bromide ions present with specimen. Then the potential level of the working electrode is cyclically changed within the second predetermined range to determine the amount of coulombs attributable to bromide ions and subsequently the amount of coulombs attributed to the chloride ions concentration is calculated by subtracting the latter from the former and finally determining both ion concentrations by referring to a calibration curve.

6 Claims, 6 Drawing Sheets

METHOD FOR CONTINUOUSLY DETERMINING CONCENTRATION OF CHLORIDE IONS AND BROMIDE IONS CONTAINED IN SERUM

INTRODUCTION AND BACKGROUND

The present invention relates to a method for determining electrochemically, quantitatively and continuously the concentration of each of chloride ions and bromide ions contained in a serum by employing one and the same serum specimen and one set of electrodes.

Hitherto, a quantitative determination of the chloride ions and bromide ions contained in a serum was measured by various methods such as ion chromatography and coulometric titration.

However, in these methods, quantitative determination of the chloride ions and bromide ions could not be measured in serum as it is, because the serum should be treated immediately after sampling, and errors caused by an interference of the chemicals used for the treatment may be introduced. Furthermore, the preparative operations for a specimen to be analyzed is complicated and skilled techniques in chemical analysis is required.

Particularly when the serum to be analyzed is blood, the blood serum should be separated from the whole blood, and thus difficult operations makes the measurement itself more complicated.

As aforementioned, up to the present invention methods for the quantitative determination of chloride ions and bromide ions contained in a serum suffered defects such as a deficiency of rapid determination and insufficient accuracy required for the analysis. Moreover it was necessary to provide a specimen and an electrode for each ion to be determined. Still further, reproducibility with a good accuracy was not readily attained.

SUMMARY OF THE INVENTION

It is an object of the invention to solve the problems and to improve defects previously encountered in the prior art.

A further object of the present invention is to avoid defects and to solve problems of a conventional measurement method and is to provide a method for determining each concentration of chloride ions and bromide ions in serum as a specimen using one and the same serum specimen and employing one set of electrodes, and being conducted continuously and quantitatively with the repeatability required in a short time by a simple and easy operation.

In attaining the above and other objects, one feature of the invention resides in a method for continuously determining the concentration of each of chloride ions and bromide ions contained in a serum by employing one and same serum specimen for said determination and by using one set of electrodes. The method comprises the steps A, B and C, discussed below.

In step (A) there is carried out a determination of the amount of coulombs of an oxidation current and reduction current, as the total amount of coulombs of chloride ions and bromide ions, obtained continuously from a current change generated corresponding to a potential change caused by cyclically changing a potential level of a working electrode in the range from $-0.5$ to $+0.5$ V vs. Ag/AgCl and then from $+0.5$ to $-0.5$ V vs. Ag/AgCl to a counter electrode. There is employed in the invention a measuring electrode assembly consisting of a working electrode made of silver, a counter electrode made of stainless steel and a reference electrode made of Ag/AgCl which is covered by a polymer film having fine porosity whereby chloride ions and bromide ions can permeate through the polymer film but coexistent materials such as proteins contained in a serum can not permeate. The electrodes are disposed into the serum specimen to be analyzed in a single vessel or tank.

In step (B), there is carried out a step of determining the amount of coulombs of an oxidation current and a reduction current, as the amount of coulombs of bromide ions contained in the serum, obtained continuously from a current change generated corresponding to a potential change caused by cyclically changing the potential level of the working electrode in the range from $-0.5$ to $+0.16$ V vs. Ag/AgCl and then from $+0.16$ to $-0.5$ V vs. Ag/AgCl to the counter electrode.

Then in step (C), there is carried out a calculation of the amount of coulombs of the chloride ions by subtracting the amount of coulombs of bromide from the total amount of coulombs of the chloride ions and bromide ions determined before. Thus each ion concentration of chloride and bromide contained in the serum can be determined quickly by comparing the measured coulombs with those obtained in previously prepared working curves.

In carrying out the method for determining chloride ions and bromide ions contained in serums, a variety of serums can be tested; for example, blood, blood serum, blood plasma, lymph, cerebrospinal fluid and saliva. Generally, the serum is diluted by a buffer solution or distilled water.

The polymer film having the fine porosity is preferably one selected from filmy materials made of polycarbonate, cellulose acetate and the like. Any suitable porous polymer can be used provided it does not interfere with the desired results or react with the components of the serum; i.e. it is inert.

Generally the polymer film has a thickness of 5 $\mu$m to 7 $\mu$m.

It has been found that the pores of the porous polymer film have a diameter of 0.03 $\mu$m or less.

DETAILED DESCRIPTION OF THE INVENTION

Figure 1:
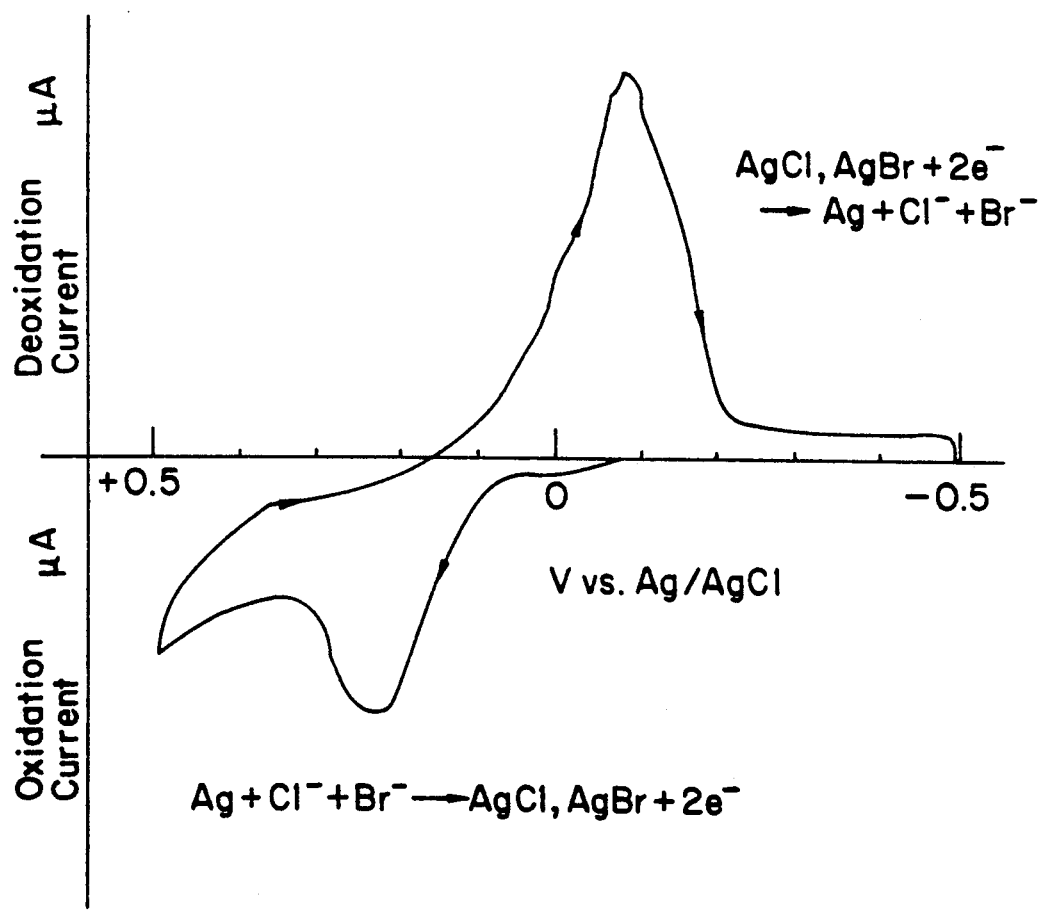
FIG. 1 is a voltammgram of an embodiment according to the present invention.

Various electrolytes are contained in a serum and among them sodium ions, potassium ions and chloride ions are most important ions. Therefore, the health condition of a human body can be evaluated by determining the ion concentrations. For example, by determining bromide ion concentration in a serum, a poisoning condition caused by chemicals containing a bromide compound can be diagnosed. Thus, the method according to the present invention has a important clinical medical significance.

The most important advantage of the method according to the present invention is the possibility of direct determination of chloride ions and bromide ions in serum by employing one and the same serum specimen as is, without any pretreatment, and employing one electrode. The serum that can be tested by the present invention include blood, blood serum, blood plasma, lymph, cerebrospinal fluid and saliva.

With respect to blood which is the most typical serum, chloride ions and bromide ions concentration can be determined in a blood specimen itself and in the blood after separating blood serum or blood plasma from the blood and further in blood serum or blood plasma separated optionally. Also, the determination can be carried out in a serum specimen diluted with a buffer solution and distilled water.

Thus the determination method of the invention is not limited to only blood but can be applied to all kinds of serums such as lymph, cerebrospinal fluid and saliva. Furthermore, the method according to the present invention can be applied to determine continuously the chloride ion and bromide ion concentration contained in not only serums of all kinds of Vertebrata and Invertebrata but also in the fluids of a botanical plant by employing one fluid and one electrode.

The second important advantage of the method according to the present invention is the construction of the measuring electrode assembly which is covered by a polymer film having a fine porosity where coexistent materials such as proteins contained in the serum can not permeate. The polymer film to be used is a film made of polycarbonate, cellulose acetate, or the like. The most preferable thickness of the film is from 5 $\mu$m to 7 $\mu$m (in micrometers). If the thickness is larger than this range the permeation of chloride ions and bromide ions are retarded resulting in the disadvantage of increasing the time required to analyze. The diameter of the fine pores in the film should be 0.3 $\mu$m or less. If the pore size is larger than this, the coexistent materials such as proteins, bilirubin and haemoglobin may permeate through the film and it may undesirably affect the analytical results.

Direct determination of chloride ions and bromide ions in a serum after sampling without any special pretreatment, can be attained by employing a measuring electrode assembly covered with a special film according to the present invention.

The third advantage of the present invention is to continuously determine chloride ion and bromide ion in one and same body liquid specimen employing one electrode by determining the amount of coulombs of oxidation current and reduction current obtained continuously from the change of the current generated corresponding to the change of potential caused by cyclically changing the potential level of the working electrode within a range from $-0.5$ to $+0.5$ V vs. Ag/AgCl and then in the range $+0.5$ to $-0.5$ V vs. Ag/AgCl to the counter electrode.

In the method according to the present invention, as aforementioned, since the electrode is covered with a specially designed polymer film with fine porosity coexistent materials such as proteins in the serum are prevented from permeation through the film. The outstanding result is that the concentration of chloride ions and bromide ions contained in serum specimen as is can be determined continuously by employing one and the same specimen, and one electrode. In a first step, the total amount of the chloride ions and bromide ions contained in the serum represented by an amount of coulomb employing a calibration curve prepared in advance is determined.

Then, in a second step an amount of coulombs of an oxidation current and a reduction current, the amount of bromide ions contained in the serum that is analyzed. This value is obtained continuously from a current change generated corresponding to a potential change caused by cyclically changing a potential level of the working electrode in the range from $-0.5$ to $+0.16$ V vs. Ag/AgCl and then from $+0.16$ to $-0.5$ V vs. Ag/AgCl to the counter electrode.

In a third step the amount of coulomb of the chloride ions is calculated by subtracting the amount of coulombs of the bromide ions from the total amount of coulombs of the chloride ions and bromide ions previously determined and determining each concentration of chloride ions and bromide ions contained in the serum employing a calibrating curve prepared in advance.

Thus the concentration of chloride ions and bromide ions in serum employing one and the same serum specimen and one electrode can be determined continuously.

AgCl and AgBr formed on the Ag electrode can be dissolved and cleaned automatically by changing cyclical way the potential level of the working electrode.

The present invention will be described in detail referring to the drawings as follow.

FIG. 1 is an embodiment of a voltammogram according to the present invention. In this case, a silver electrode was used as a working electrode and a blood serum was prepared by JOKO Co., Ltd. The chloride ions and bromide ions are contained in the specimen blood serum. It is shown graphically as an oxidation current wave and a reduction current wave obtained continuously from a current change generated corresponding to a potential change caused by cyclically changing a potential level of the working electrode in the range from $-0.5$ to $+0.5$ V vs. Ag/AgCl and then in the range from $+0.5$ to $-0.5$ V vs. Ag/AgCl to the counter electrode. From this voltammogram as shown in FIG. 1, the total concentration of chloride ions and bromide ions contained in the serum was determined as an amount of coulombs.

Figure 2:
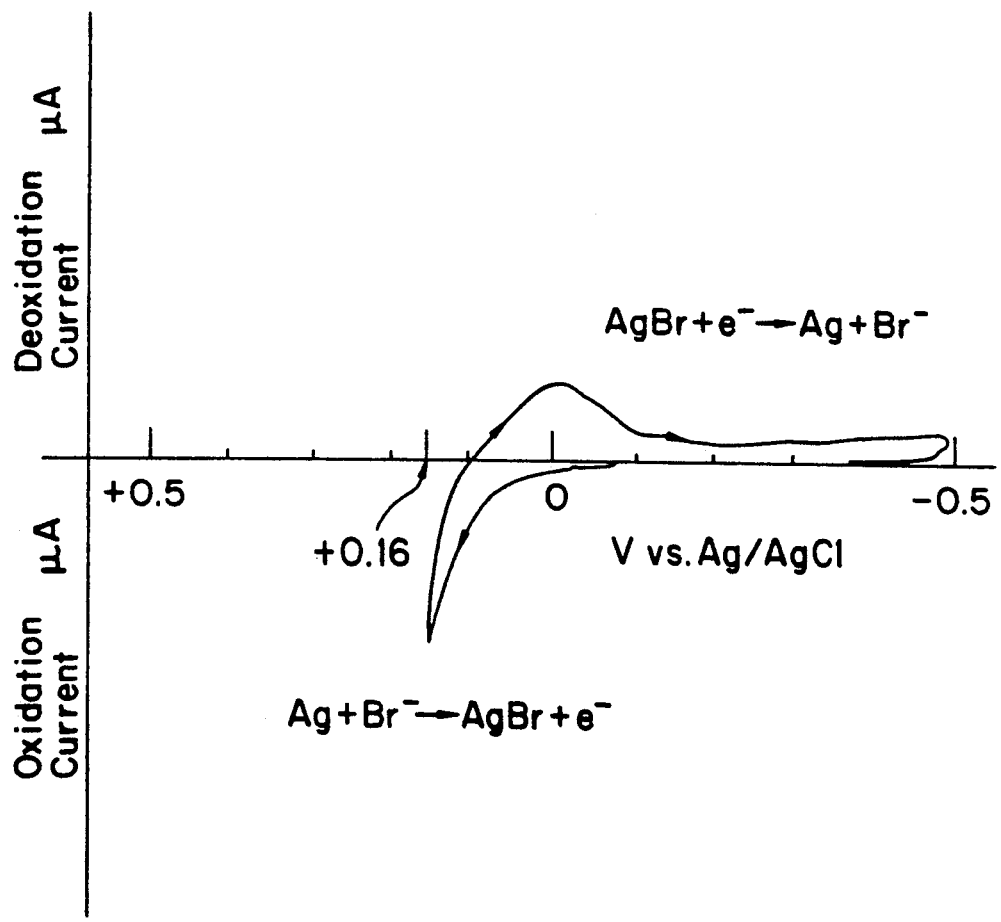
FIG. 2 is a voltammgram of an embodiment according to the present invention showing an amount of coulomb of bromide ions.

In FIG. 2 the bromide ion concentration is graphically shown as an oxidation current and reduction current, obtained continuously from a current change generated corresponding to a potential change cause by cyclically changing a potential level of the working electrode in the range from $-0.5$ to $+0.16$ V vs. Ag/AgCl and then from $+0.16$ to $-0.5$ V vs. Ag/AgCl to the counter electrode.

Figure 4:
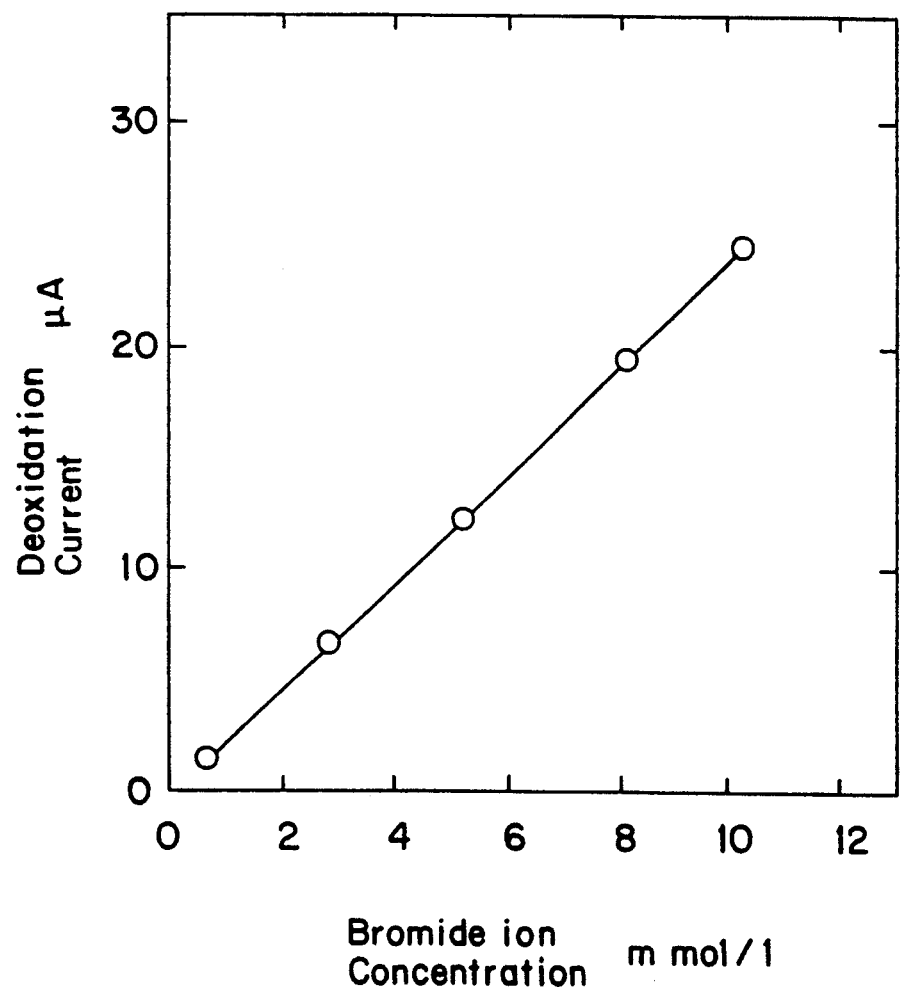
FIG. 4 is calibration curve for bromide ions.

FIG. 4 is a calibration curve prepared in advance. The bromide ion concentration is determined from the amount of coulombs obtained from FIG. 2 referring to the calibration curve in FIG. 4.

The concentration of chloride ions in the specimen was determined as the amount of coulombs obtained by subtracting the amount of coulombs representing the bromide ion concentration from the amount of coulombs attributed to the total amount of chloride ions and bromide ions.

Figure 5:
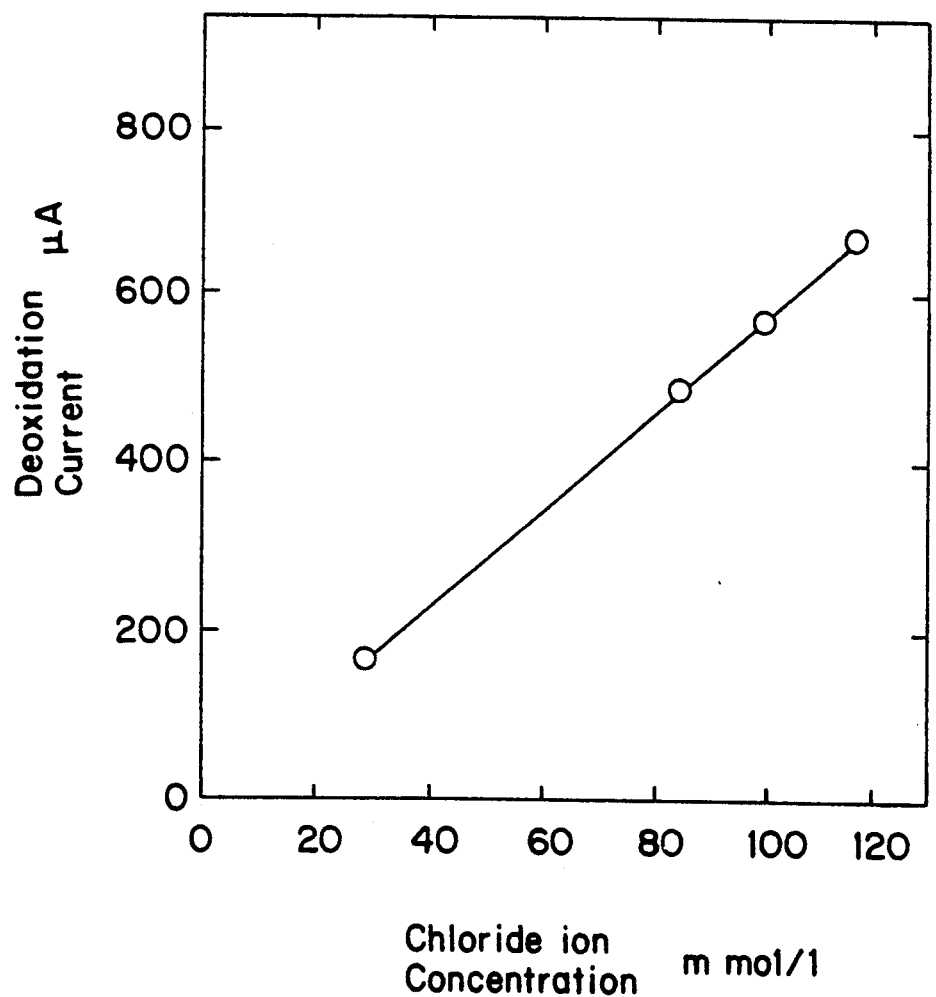
FIG. 5 is a calibration curve for chloride ions.

FIG. 5 is a calibration curve from chloride ion prepared in advance.

Figure 3:
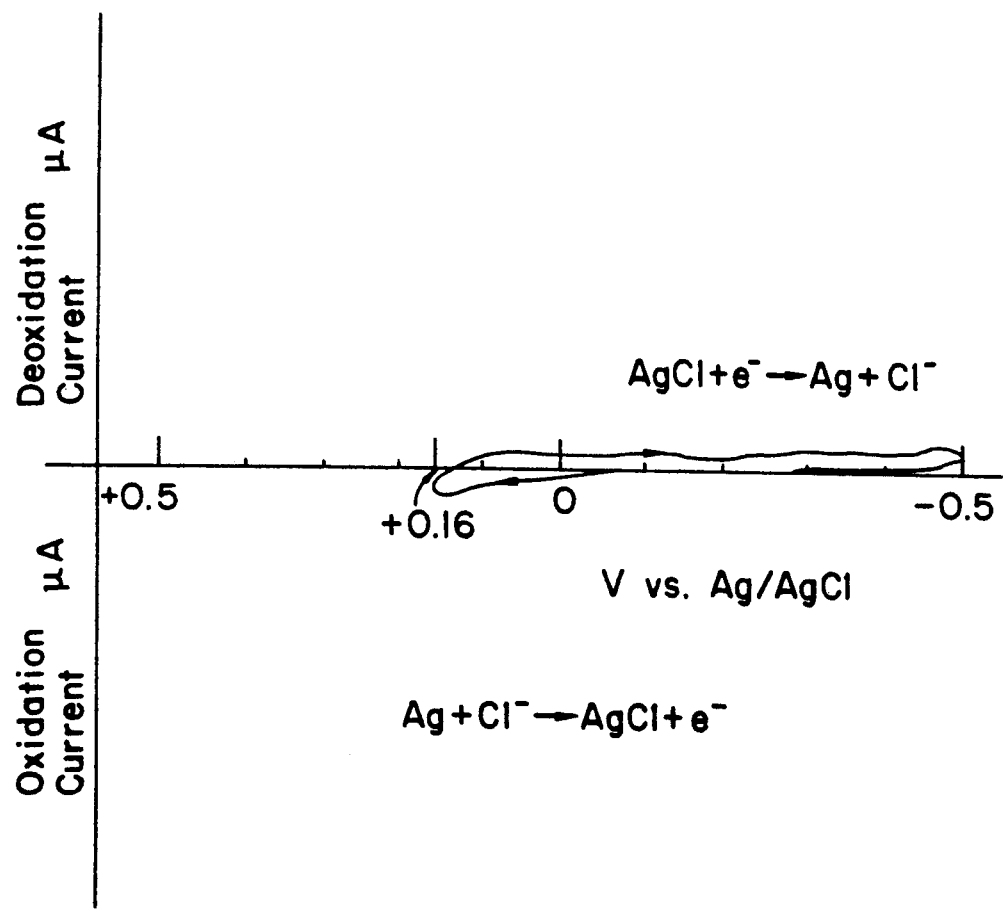
FIG. 3 is a voltammgram of an embodiment according to the present invention showing an embodiment of coulomb of chloride ions.

FIG. 3 shows the amount of coulombs of chloride ion concentration which is drawn as an oxidation current and a reduction current, obtained continuously from a current change generated corresponding to a potential change caused by cyclically changing a potential level of the working electrode in the range from −0.5 to +0.16 V vs. Ag/AgCl and then from +0.16 to −0.5 V vs. Ag/AgCl to the counter electrode. However, a similar reaction as the case of the amount of coulombs for chloride ions as before was not observed in the cycle of the range from −0.5 to +0.16 V vs. Ag/AgCl and then from +0.16 to −0.5 V vs. Ag/AgCl, thus it is not affect by chloride ions.

Similarly, it was found that the amount of coulomb attributed to bromide ions is not affected by chloride ions as shown in FIG. 2.

Figure 6:
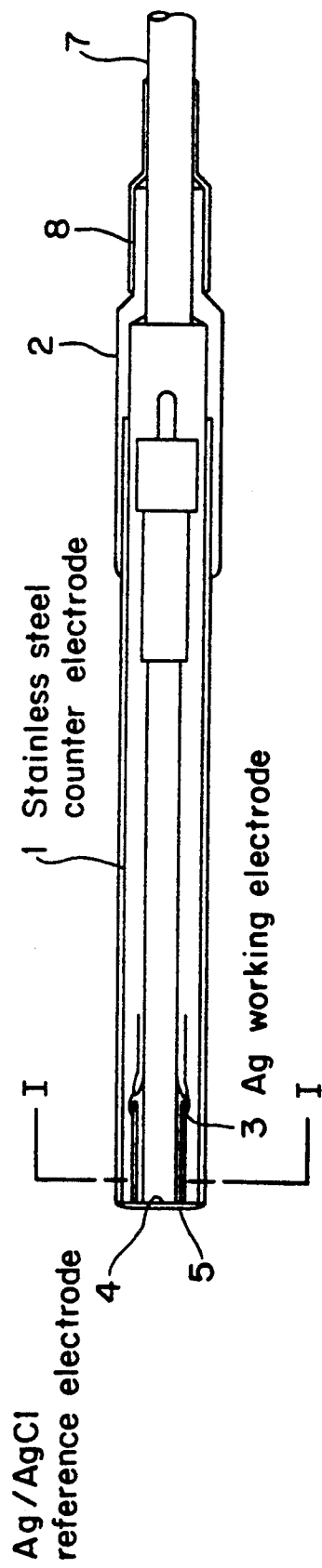
FIG. 6 is a schematic cross section of a measuring electrode assembly of the invention.
Figure 7:
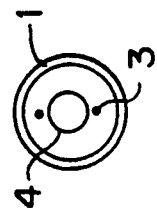
FIG. 7 is a schematic cross section of the measuring electrode assembly along the line I—I shown in FIG. 6.

FIGS. 6 and 7 show a measuring electrode assembly composed of a counter electrode (1), an Ag working electrode (3) and a reference electrode (4). A polymer film 5 covers the measuring electrode assembly. Supporting rods (7) and sheaths 2 and 8 are provided for their cited purpose.

RESULTS OF EXAMINATION

The reproducibility or the determination of chloride ions and bromide ions on the blood serum made of JOKO Co., Ltd. is shown in Table 1.

TABLE 1

| Measurement Sample No. | Chloride ion Concentration (m mol/L) | Bromide ion Concentration (m mol/L) |
|---|---|---|
| 1 | 119.4 | 8.0 |
| 2 | 119.3 | 8.3 |
| 3 | 119.3 | 8.2 |
| 4 | 119.4 | 8.3 |
| 5 | 120.2 | 8.1 |
| 6 | 119.7 | 8.2 |
| 7 | 119.7 | 8.2 |
| 8 | 119.5 | 7.8 |
| 9 | 119.8 | 8.0 |
| 10 | 119.7 | 8.0 |

(Note) Number of determinations = 10

| | chloride ion concentration | bromide ion concentration |
|---|---|---|
| mean value = | 119.60 m mol/L | 8.10 m mol/L |
| standard deviation = | 0.27 m mol/L | 0.15 m mol/L |
| coefficient of variation = | 0.23% | 1.8% |

The determination was carried out successively in one reaction tank without washing of electrode.

As seen above, the measurement according to the present invention exhibits remarkably good reproducibility in the repeated determinations. On the other serum an outstanding reproducibility as the above was attained.

In summary, the operational principal for the present analysis is based on the following reactions and procedures. When an Ag electrode is linearly swept between a given potential region (−0.5∼+0.5V vs. Ag/AgCl), $\bar{Cl}$ and $\bar{Br}$ in the serum react with the Ag electrode resulting in the following reactions: $Ag + \bar{Cl} + \bar{Br} \rightarrow AgCl, AgBr + 2e$ (anodic); and $AgCl, AgBr + 2e \rightarrow Ag + \bar{Cl} + \bar{Br}$ (cathodic). Based on these reactions, the sum of the reduction current $I_{Cl+Br}$ due to AgCl and AgBr was measured. The potential of the Ag electrode was then swept between the region of −0.5∼+0.16 V vs. Ag/AgCl. Under these conditions, only $\bar{Br}$ reacts with the Ag electrode resulting in the following reactions; $Ag + \bar{Br} \rightarrow AgBr + 1e$ (anodic); and $AgBr + e \rightarrow Ag + \bar{Br}$ (cathodic). The reduction current of these reactions, $I_{Br}$, was then measured this makes it possible to measure the reduction current due to Cl, $I_{Cl}$, by subtracting the current $I_{Br}$ from $I_{Cl+Br}$. The concentration of $\bar{Cl}$ and $\bar{Br}$ in the serum can be determined quickly by comparing the measured current ($I_{Cl}$ and $I_{Br}$) with those obtained in previously prepared working curves.

The assay precision and repeatability for $\bar{Cl}$ and $\bar{Br}$ were well below O.V. 1.5%. Comparison studies between the proposed method and coulometric titration method resulted in a good correlation for the serum samples. The correlation coefficient (r) was 0.987 with linear regression Y−0.999X+1.3 for $\bar{Cl}$ and 0.973 with Y=1.001X+0.1 for $\bar{Br}$. Analysis rate was 60 samples per hour.

By the method according to the present invention, employing one and the same serum specimen and one electrode, each concentration of chloride ions and bromide ions contained in a serum can be determined rapidly, continuously and accurately.

What is claimed is:

1. A method for continuously determining each concentration of chloride ion and bromide ion contained in a serum by employing one and the same serum specimen comprising the steps of
   (A) providing a measuring electrode assembly consisting of working electrode made of silver, a counter electrode made of stainless steel and a reference electrode made of Ag/AgCl which is covered by a polymer film with fine porosity which permits chloride ions and bromide ions to permeate said film but coexistent materials in a serum can not permeate, disposing said measuring electrode assembly in a serum specimen to be analyzed in one tank, determining the amount of coulombs of an oxidation current and reduction current, as the total amount of coulombs of chloride ions and bromide ions, obtained continuously from a current change generated corresponding to a potential change caused by cyclically changing a potential level of the working electrode in the range from −0.5 to +0.5 V vs. Ag/AgCl and then from +0.5 to −0.5 V vs. Ag/AgCl to a counter electrode,
   (B) determining the amount of coulombs of an oxidation current and a reduction current, as the amount of coulombs of bromide ions contained in said serum, obtained continuously from a current change generated corresponding to a potential change caused by cyclically changing a potential level of the working electrode in the range from −0.5 to +0.16 V vs. Ag/AgCl and then from +0.16 to −0.5 V vs. Ag/AgCl to the counter electrode, and
   (C) calculating an amount of coulombs of the chloride ions by subtracting the amount of coulombs of bromide ions from the total amount of coulombs of the chloride ions and bromide ions determined before and determining each ion concentration of chloride and bromide contained in said serum by comparing the measured coulombs with those obtained in previously prepared working curves.

2. The method according to claim 1 wherein said serum is one selected from the group consisting of whole blood, blood serum, blood plasma, lymph, cerebrospinal fluid and saliva.

3. The method according to claim 1 wherein said serum is diluted by a buffer solution or distilled water.

4. The method according to claim 1, wherein said polymer film with fine porosity is made of polycarbonate or cellulose acetate.

5. The method according to claim 1 wherein said polymer film has a thickness of 5 μm to 7 μm.

6. The method according to claim 1 wherein the diameter of fine pores provided in said polymer film is 0.03 μm or less.

* * * * *